United States Patent [19]

Yu et al.

[11] Patent Number: 5,487,746
[45] Date of Patent: Jan. 30, 1996

[54] SURGICAL CLIP HAVING A LONGITUDINAL OPENING THROUGH WHICH CLAMPED TISSUE PROTRUDES

[76] Inventors: George W. Yu, 1326 Bayhead Rd., Annapolis, Md. 21401; H. Logan Holtgrewe, 473 Fair Oak Dr., Severna Park, Md. 21146

[21] Appl. No.: 347,081

[22] Filed: Nov. 23, 1994

[51] Int. Cl.⁶ ..................................................... A61B 17/04
[52] U.S. Cl. .......................... 606/151; 606/157; 24/326; 24/115 A; 24/703.1
[58] Field of Search .................................... 606/143, 151, 606/157, 158; 24/115 A, 326, 703.1

[56] References Cited

U.S. PATENT DOCUMENTS

| | | |
|---|---|---|
| 600,887 | 3/1898 | Pettit . |
| 2,626,608 | 1/1953 | Garland . |
| 3,270,745 | 9/1966 | Wood . |
| 3,363,628 | 1/1968 | Wood . |
| 3,604,067 | 9/1971 | Brown ........................................ 24/326 |
| 3,705,586 | 12/1972 | Sarracino . |
| 3,856,016 | 12/1974 | Davis . |
| 3,867,944 | 2/1975 | Samuels . |
| 4,188,953 | 2/1980 | Klieman et al. ......................... 606/157 |
| 4,509,518 | 4/1985 | McGarry et al. ....................... 606/143 |
| 4,702,247 | 10/1987 | Blake, III et al. ....................... 606/157 |
| 4,765,335 | 8/1988 | Schmidt et al. ......................... 606/157 |
| 4,799,481 | 1/1989 | Transue et al. .......................... 606/157 |
| 4,844,066 | 7/1989 | Stein ....................................... 606/157 |
| 4,976,722 | 12/1990 | Failla . |
| 5,171,252 | 12/1992 | Friedland ................................ 606/151 |
| 5,201,746 | 4/1993 | Shichman ................................ 606/151 |
| 5,441,509 | 8/1995 | Vidal et al. .............................. 606/157 |

FOREIGN PATENT DOCUMENTS 1389762  4/1988  U.S.S.R. .

OTHER PUBLICATIONS

Information Booklet for "Auto Suture Premium Surgiclip Disposable Automatic Clip Applier", Manufactured by United States Surgical Corporation, Copyright 1992.

How Secure are Laparoscopically Placed Clips? An In Vitro and In Vivo Study M. Timothy Nelson, MD; Masanobu Nakashima, MD; Sean J. Mulvihill, MD, Arch Surg–vol. 127, Jun. 1992.

*Primary Examiner*—Gary Jackson
*Attorney, Agent, or Firm*—Oblon, Spivak, McClelland, Maier & Neustadt

[57] ABSTRACT

A surgical clip having a double-leg side and a single-leg side. When the surgical clip is closed, the movement of the single-leg side towards the double-leg side displaces the tissue being clamped through a longitudinal opening between the legs forming the double-leg side. In order to increase the gripping area of the clip, the gripping surface of the single leg is a rounded wedge shape with smooth edges (not sharp) which are parallel to the inboard side of the double legs. The rounded wedge shape is used in order to avoid cutting the clamped tissue. When the surgical clip engages with tissue to be clamped, a plane of the tissue is displaced at the clamping region which increases the force needed to displace the clip from the tissue being clamped.

22 Claims, 5 Drawing Sheets

(RRIOR ART)

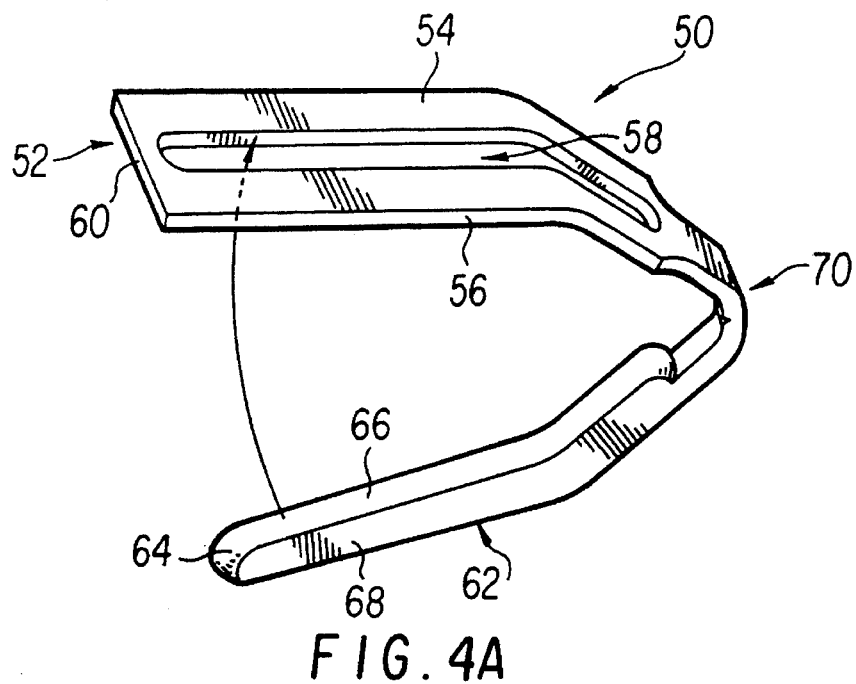
FIG. 4A
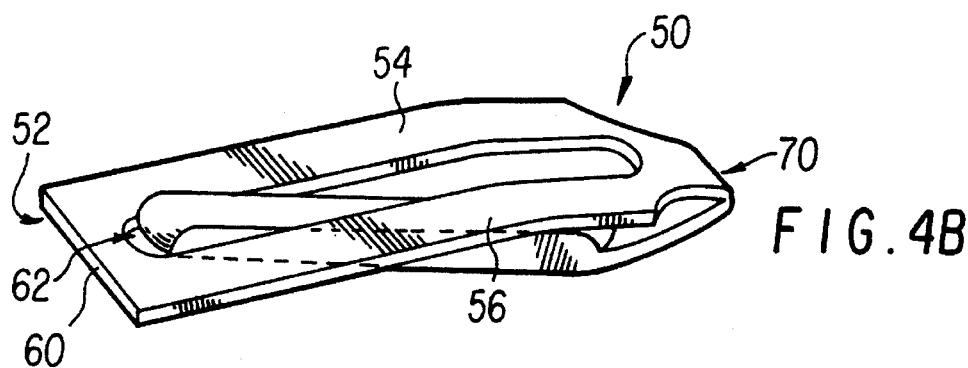
FIG. 4B
FIG. 4C
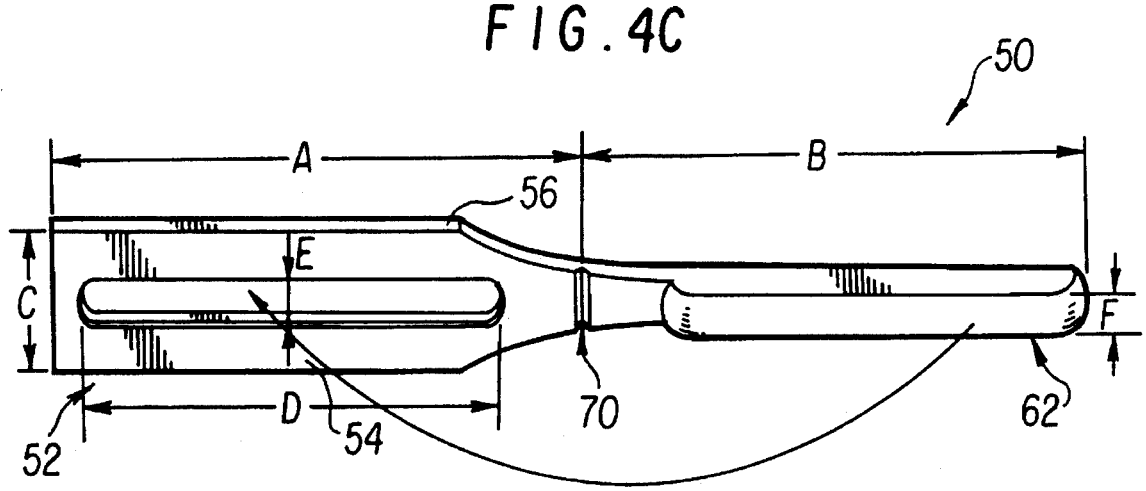

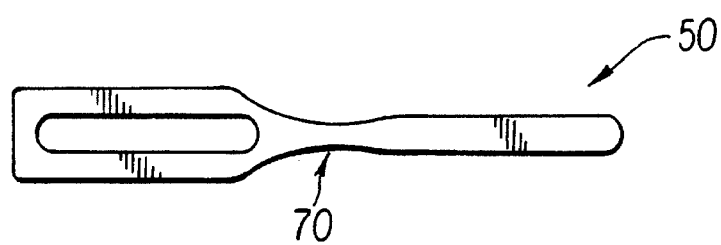
FIG.9A
FIG.9B
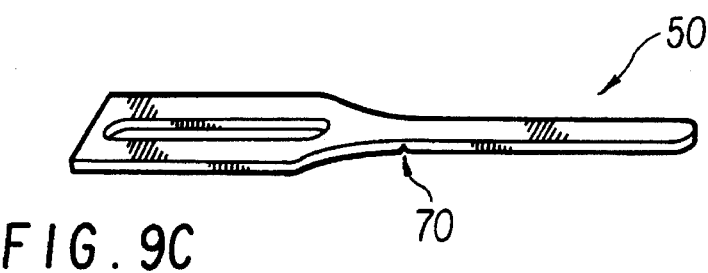
FIG.9C
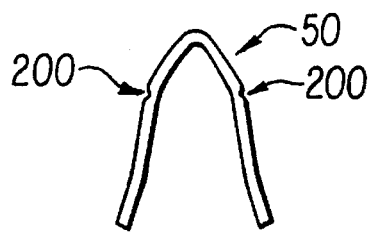
FIG.9D
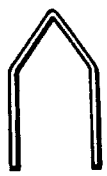   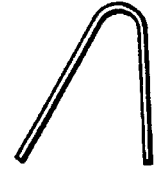      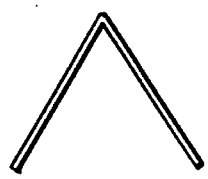
FIG.10A  FIG.10B  FIG.10C  FIG.10D

SURGICAL CLIP HAVING A LONGITUDINAL OPENING THROUGH WHICH CLAMPED TISSUE PROTRUDES

BACKGROUND OF THE INVENTION

1. Field of the Invention

The invention relates to surgical clips used to occlude or ligate body tissues, such as blood vessels, lymphatic vessels and combinations of blood or lymphatic vessels imbedded in fat, muscle, fascia and visceral organs in surgical procedures both in conventional "open" operations and laparoscopic surgery.

2. Discussion of the Background

Traditionally, when ligation of vessels was required during surgery, one used "ties" (sutures alone) or stitches (sutures with a needle) to ligate divided blood vessels. With the increasingly popular laparoscopic surgery in which several small incisions are used to gain access to the abdominal cavity of the patient, it is much more difficult to use traditional tying or stitching (using sutures) to ligate vessels than in the classic "open" surgery in which a large incision is made in the patient.

Surgical clips, sometimes referred to as hemostatic or ligation clips are known, commercially available and an alternative to the use of sutures. These surgical clips are sold, for example, under the trade names Ligaclip and Hemoclip by Ethicon, Weck, and U.S Surgical. Essentially, Hemoclips or Ligaclips are the same and both occlude and ligate or close off blood and lymphatic vessels to prevent bleeding and lymph fluid leakage. In the present writing, the term "surgical clip" refers to a device to clamp and close-off (occlude and ligate) any type of tissues and/or vessels and will have applications which are the same or similar to the applications of both Hemoclips and Ligaclips.

FIG. 1 illustrates a conventional commercially available surgical clip such as the Ligaclip by Ethicon. This clip has a V-shaped configuration with legs 2 and 4 joined at an apex 6 which operates as a hinge. The legs 2 and 4 are spaced apart, usually at a 45°–90° angle from the hinge or apex. The conventional clip illustrated in FIG. 1 has a longitudinal groove and diagonal cuts on the clamping surface 8, a wedged-out section 10 for ease of bending, and protrusions 12 which provide a gripping surface for ease of application of the clip.

A common problem with conventional surgical clips is the slippage off the tissues or vessels. FIG. 2A illustrates a conventional clip having legs 2 and 4 enclosing tissue T in an unclamped state. FIG. 2B illustrates the conventional surgical clip in a clamped state around the tissue T. However, the configuration illustrated in FIG. 2b does not provide a very strong clamping force and the tissue T may slide or slip relative to the clip either longitudinally through the opening of the clip which is opposite to the apex or hinge 6 (i.e., the tissue slips off the legs of the clip), or slide transverse to the length of the clip (i.e., the clip slides along the length of the tissue). This means that the clip may slide horizontally or vertically of the intended occluded tissues. A test published in the article "How Secure Are Laparoscopically Placed Clips? An in Vitro and in Vivo Study" by M. T. Nelson et al, appearing in the publication "Archives of Surgery", Vol. 127, Jun. 19, 1992, determined that conventional commercially available surgical clips such as the Endo Clip or the Ligaclip are transversely (horizontally) dislodged with a mean force of 1.8–2.7 Newtons and axially or longitudinally (vertically) dislodged with a force of 4.0–4.8 Newtons.

In order to increase the security of surgical clips and prevent the clips from being dislodged, there have been numerous attempts to modify the shape/texture of the gripping surface of the clips in order to decrease the chances of the clip dislodgement. One such variation in the gripping surface of the clips is illustrated in FIGS. 3A and 3B in which a protrusion 20 is placed on one leg of the clip while a groove 22 is placed on the opposite leg of the clip. The unclamped and clamped states of such a clip are illustrated in FIGS. 3A and 3B respectively. Such a protrusion and groove structure can be seen in U.S. Pat. Nos. 4,976,722 and 600,887. Other variations of the gripping surface are shown in U.S. Pat. Nos. 4,799,481, 4,844,066, and 5,201,746. While these known alternatives to the gripping surfaces may improve the stability of surgical clips, the available surgical clips are still considered to be only marginally successful and often, two clips are used to provide added security to the occlusion of the vessel.

SUMMARY OF THE INVENTION

Accordingly, one object of this invention is to provide a novel surgical clip which will maintain its closed state without tissue slippage under conditions where conventional types of surgical clips open and/or slip off. It is a further object to provide a surgical clip which is both secure and resistant to slippage yet can be applied quickly and easily. It is still another object of the invention to provide a secure surgical clip without the need for a specific locking mechanism which must be engaged in order to secure the surgical clip.

These and other objects are accomplished by a novel surgical clip. The first embodiment of the surgical clip has three legs which when opened to a flat position has the shape of the letter "Y" and therefore, the first embodiment is referred to as the "True Y Clip". In the first embodiment, two legs are on one side of the apex or hinge of the clip and one leg is on the other side. A longitudinal opening is formed between the two legs on the same side of the clip. In its open state, the legs are open between approximately a 45°–90° degree angle at the apex in the form of the letter "V". When the clip is in its closed state, the single leg and double leg are compressed into each other such that the single leg approaches or at least partially protrudes into the longitudinal opening of the double leg. The preferred configuration of the first embodiment is to have the two legs on the same side fused at their distal ends so that the longitudinal opening between is securely formed. However, a variation of the first embodiment allows the two legs on the same side to be unconnected at their distal ends.

The preferred shape of the clamping surface of the leg on the one-leg side of the clip is a smooth rounded wedge with the pinnacle of the rounded wedge facing towards the center of the longitudinal opening. The edges of the wedge configuration are smooth and not sharp to avoid cutting the tissue. The preferred shapes of the clamping side of the two legs of the two-leg side of the clip are angled such that the planes of the inboard clamping surfaces of the legs of the two-leg side of the clip are parallel to the corresponding clamping surface of the single leg in order to increase the gripping surface area.

When clamping, the surgical clip is bent at the apex or hinge of the clip, and the legs are compressed against biological tissues between. This pushes the biological tissues through the longitudinal opening of the two-leg side of the clip by the single leg of the clip. The tissues being clamped are compressed and also extruded through the longitudinal opening. Therefore, the clamping force of the invention is not only provided by the tissues engaging the three legs of the clip, but an island of tissue is pushed by the single leg and trapped within the opening of the double-leg side of the clip. The edges are smooth and do not cut or lacerate the compressed tissues.

The second embodiment of the invention has the same basic shape of the first embodiment but is smaller than the first embodiment and therefore, suitable for use in laparoscopic as well as open surgery. As the second embodiment has a small size and retains the Y-shape of the first embodiment, the second embodiment is referred to as the "Micro Y Clip". Due to the smaller size of the second embodiment as compared to the first embodiment, the shape of the clamping surfaces of each of the three legs of the second embodiment may be flat instead of having a wedge shape. As in the first embodiment, the single leg of the second embodiment fits into the longitudinal opening between the two-leg side of the clip to provide the clamping force.

The third embodiment of the invention has the width of the single leg side of the clip being approximately equal to the width of the double-leg side of the clip and has a longitudinal ridge on the single leg side of the clip which mates with the longitudinal opening of the double-leg side. This allows a similar clamping effect to occur in the third embodiment as occurs in the first and second embodiments. The third embodiment is referred to by the inventors as the "Even Y Clip" because the width of each side of the clip is equal.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 4A illustrates a surgical clip according to the first embodiment of the invention in its normal open state;

FIG. 4B illustrates the surgical clip of the first embodiment in its closed state;

FIG. 4C illustrates a surgical clip according to the first embodiment which is opened to be flat in order to show the dimensions of the clip;

FIG. 9A illustrates the hinge portion of a clip having a narrow waist;

FIGS. 9B and 9C illustrate the hinge portion of the clip respectively having a rounded shape and a V-shape;

FIG. 9D illustrates the outside portions of the legs of the clip having an indentation; and FIGS. 10A–10D illustrate various shapes of the invention.

DESCRIPTION OF THE PREFERRED EMBODIMENTS

Figure 1:
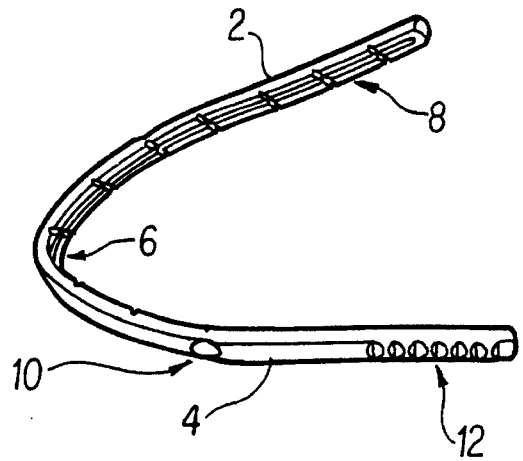
FIG. 1 illustrates a conventional surgical clip.
Figure 2A:
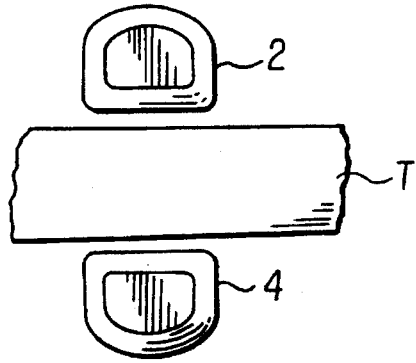
FIGS. 2A and 2B illustrate the surgical clip of FIG. 1 in an unclamped and clamped state respectively.
Figure 2B:
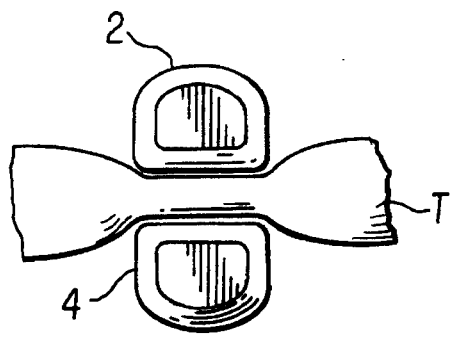
Figure 3A:
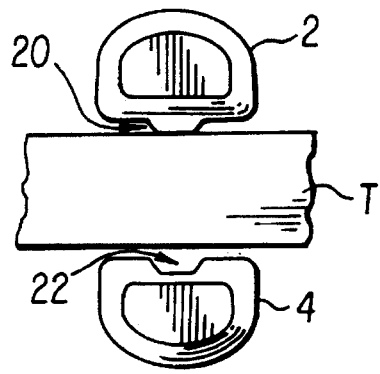
FIGS. 3A and 3B illustrate a conventional surgical clip with enhanced gripping surfaces including a protrusion and groove in an unclamped and clamped state respectively.
Figure 3B:
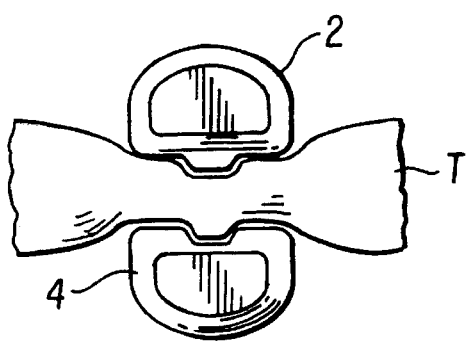

Referring now to the drawings, wherein like reference numerals designate identical or corresponding parts throughout the several views, and more particularly to FIG. 4A, there is illustrated a surgical clip 50 constructed according to the first embodiment of the invention in its normal open state. The clip 50 has a double-leg side 52 and a single-leg side 62 which are connected to one another through a hinge region 70, also referred to as an apex.

The double-leg side is composed of two legs 54 and 56 which are connected to each other at the hinge region 70 and have a longitudinal opening 58 therebetween. The preferred embodiment of the invention has the legs 54 and 56 fused at region 60 which are the distal ends of the legs but a variation of the invention can operate without the legs being fused at their distal ends. The single-leg side of the clip contains leg 62 which is connected to the hinged region 70.

Figure 6:
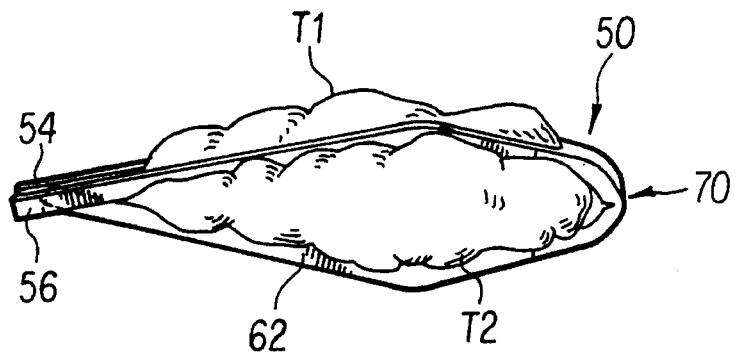
FIG. 6 illustrates a cross-sectional view of the first embodiment of the invention clamping tissue.

The entire clip 50 is preferably one piece of material such as stainless steel, titanium, or other suitable material and therefore considered to be a unitary device. Therefore, the hinged region 70 will ordinarily not be a hinge which pivots on a pin but will simply be a bend in the material forming the hinge. When the surgical clip is closed on the material to be clamped such as pliable biological tissues including blood vessels, lymphatic vessels, combinations of vessels and lymphatics with muscles, fat, facia, and visceral organs (i.e., liver, spleen, lung, etc.), the clip is held in its closed state by a bending of the material around the hinged area 70. In conventional clips, the holding strength results in the bend at the hinged region or crotch of the clip. If the convention clip is slightly opened at the hinged region, the legs will be opened to a much greater degree. The present invention achieves part of its holding strength from the bend at the hinge, but a slight opening of the hinge does not cause a great loss in clamping strength. Even with a slight opening of the clip, the distal end of the single leg will remain within the longitudinal opening. The slight opening results from the tissue being clamped within the clip, as illustrated in FIG. 6, which will prevent the clip from being completely closed. The present invention also gains clamping strength from tissue protruding through the longitudinal opening.

The preferred shape of the clamping surface of the single leg 62 is a rounded wedge but may be triangular. Further, the clamping surface is not required to have the preferred shape and may take on another shape such as a square or rectangle, for example. The center 64 of the clamping surface of the single leg 62 separates the clamping surface into a side 66 and a side 68. Side 66 is angled to engage with a substantially parallel clamping surface of leg 54 and side 68 similarly engages with leg 56. A cross-sectional view of the preferred shapes of the clamping surfaces of the legs of the surgical clip will be explained below with respect to FIGS. 5A and 5B.

FIG. 4B illustrates clip 50 which is the first embodiment of the invention in a closed position without any tissue being clamped. In FIG. 4B, it can be seen that the single leg 62 protrudes through the opening 58 formed between legs 54 and 56. It is to be noted that during normal operation of the surgical clip, it is preferred that the single leg 62 slightly protrude through the distal end of the opening 58 in order to achieve maximum holding power. However, the invention still operates if the leg 62 enters the opening 58 but does not protrude through it. Further, if the clip is not completely closed, the leg 62 will not enter the opening 58 and some clamping force on the tissue may be obtained but the holding power of the clip when applied in this manner will be less than if the leg entered into or protruded through the opening. As can be seen in FIG. 4B, the single leg 62 must be shorter than the lengths of the double-side legs 54 and 56 in order to enter into the opening 58. Also, if the single leg 62 is to enter the longitudinal opening, the portion which enters the opening must be narrower than the width of the longitudinal opening and the length of the single leg must be shorter than the length of the opening.

The present invention is applied using conventional devices for applying surgical clips such as a pneumatic or mechanical applicator and may be applied by a device such as the applicator disclosed in U.S. Pat. No. 4,509,518, which is incorporated herein by reference, or any commercially available surgical clip applicator such as any model Auto Suture Premium Surgiclip applier by United States Surgical Corporation including Premium Surgiclip models S-9.0", M-9.75", M-11.5", and L-13.0", the AcuClip OMS-A8 applier by Lilly, or the Endo Clip ML applier by United States Surgical Corporation, each of which is incorporated herein by reference. As the clip is applied with conventional applicators, there is no specific locking means which must be engaged in order to close and secure the surgical clip but the bending of the surgical clip around the desired tissue is the manner in which the clip is secured. As the clip is secured using a known applicator, the open angle of the clip and cross-sectional shape of the clip may be similar to the normally open angle and cross-sectional shape of conventional clips such as the Ligaclip. In addition to the conventional automatic multiple clip applicator, the present invention may applied by a single clip manual applicator.

FIG. 4C illustrates the surgical clip 50 according to the first embodiment of the invention opened beyond the normally opened state to a planar configuration and resting on its side. The shape of the single leg 62 is seen to be triangular or rounded wedge-shaped and the inboard clamping surfaces of the legs 56 and 54 are angled to be substantially parallel to the clamping surfaces of the single leg 62 when the clamp is in the closed position. The edges of the clip are smooth and not sharp in order to avoid cutting the tissue.

FIG. 4C illustrates the first embodiment of the invention spread open to flat configuration in order to show the dimension of the clip which are given in inches below. The length A of the legs 56 and 54 is 0.50" and the length B of the single leg 62 is 0.40". The width C of the two double legs is 0.125" and the length D of the longitudinal opening is 0.450". The width E of the longitudinal opening is 0.060" and the width F of the single leg is 0.045". The hinged region 70 which is open from 45°–90° has a width of 0.045". However, the clamp in its open position may have any of the shapes illustrated in FIGS. 10A–10D which are explained below. When the hinged region is narrowed as illustrated in FIG. 9A, the width of the hinged region is 0.03". Both of the double legs 56 and 54 have their clamping inboard surfaces angled at 45° for 0.015" although it is possible to extend this angle across the entire width of the single leg as is illustrated for surfaces 66 and 68 in FIG. 5A. This angle smooths the edges of the clamping surfaces in order to avoid cutting the clamped tissue. The thickness of the single leg 62 is 0.28" and the thickness of each of the double legs is 0.045". The dimensions of the clips are given to show the preferred size of the clips and are not to limit the scope of the invention beyond what is recited in the claims. The entire dimensions of the clip or individual parts of the clip may deviate by up to 50% or more than the preferred dimensions, as long as the clip continues to function with the desired holding strength.

Figure 5A:
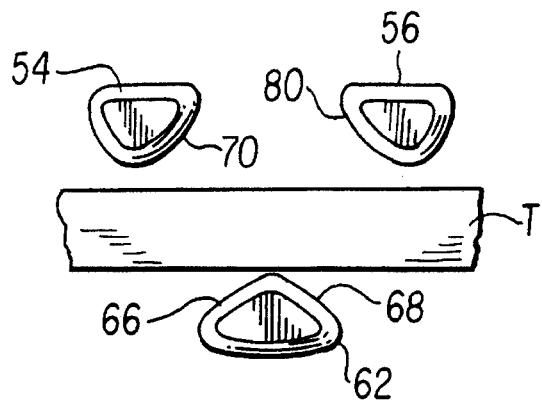
FIGS. 5A and 5B illustrate a cross-sectional view of the legs of the surgical clip of the first embodiment of the invention in an unclamped and clamped state respectively.
Figure 5B:
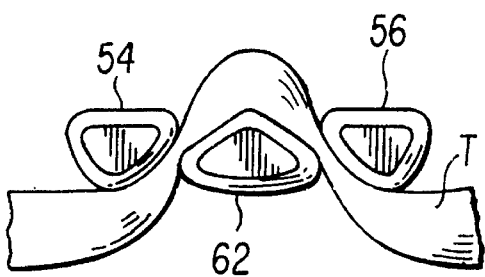

FIGS. 5A and 5B illustrate a cross-sectional view of the preferred surgical clip according to the first embodiment of the invention before and during a clamping operation of tissue T. In FIG. 5A, the double-leg side is above the tissue T and surface 70 of leg 54 and surface 80 of leg 56 will engage respectively with surfaces 66 and 68 of the single leg 62 when the clip is closed around the tissue T, as illustrated in FIG. 5B. FIG. 5B clearly illustrates that there is a planar displacement of the tissue upwardly into a second plane different from the plane of the unclamped tissue as the single leg 62 moves upwardly to engage with the double-legs 54 and 56. Further, the surface area of the tissue T which is gripped by the surgical clip is greatly increased and nearly doubled as compared to the clips which are illustrated in FIGS. 1–3B.

FIG. 6 illustrates a side view of the clip 50 according to the first embodiment of the invention when the clip is clamping tissue in the preferred manner. Tissue T1 is protruding through the longitudinal hole between the double legs 54 and 56 and tissue T2 is protruding between the single leg 62 and the double leg 56. However, depending on the manner in which the clip is applied, the single leg 62 can be extended into the longitudinal opening without protruding therethrough or only approaches the longitudinal opening without actually entering the longitudinal opening. FIG. 6 shows that by the positioning of the distal end or leg 62 into the longitudinal opening, the clip cannot be pulled longitudinally off of tissue. Further, the protrusion of tissue through the longitudinal opening prevents the clip from sliding horizontally along the length of the tissue.

Figure 7:
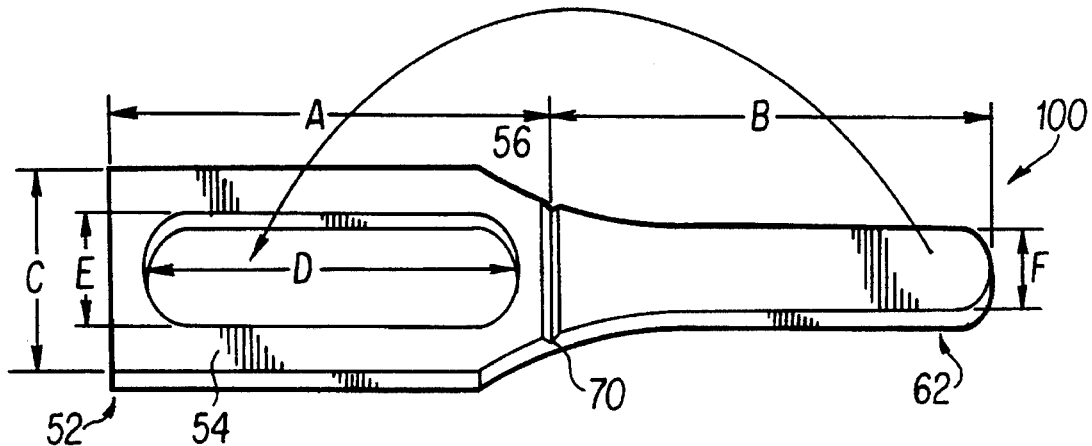
FIG. 7 illustrates the second embodiment of the invention.

FIG. 7 illustrates the second embodiment of the invention which is opened to a planar state which is beyond the normal opened state. The second embodiment of the invention is similar to the first embodiment of the invention except that the gripping or clamping surfaces of each of the double-legs 56 and 54 and the single leg 62 are planar and not angularly shaped as illustrated in the cross-sectional view of the first embodiment of the invention in FIGS. 5A and 5B. Additionally, the size of the second embodiment of the invention is smaller than the first embodiment and this smaller size allows a superior gripping strength to be achieved, even without the angularly shaped gripping surfaces, as illustrated in FIG. 5B. The second embodiment of the invention possesses the same advantages as discussed with respect to the first embodiment.

The second embodiment of the invention, due to its smaller size and ease of application in laparoscopic surgery, is referred to as the "Micro Y Clip". The dimensions of the various parts of the second embodiment of the invention are as follows. The length A of the legs 56 and 54 is 0.225" and the length B of the single leg 62 is 0.20". The width C of the two double legs is 0.125" and the length D of the longitudinal opening is 0.220". The width E of the longitudinal opening is 0.060" and the width F of the single leg is 0.045". The hinged region 70 which is open from 45°–90° has a width of 0.50", although this will be smaller if the hinged region is narrowed as illustrated in FIG. 9A. The thickness of the single leg 62 is 0.28" and the thickness of each of the double legs is 0.28". The entire dimensions of the clip or individual parts of the clip may deviate by up to 50% or more than the preferred dimensions, as long as the clip continues to function with the desired holding strength. Clip 100 is applied in the same as the manner in which clip 50 is applied.

Figure 8A:
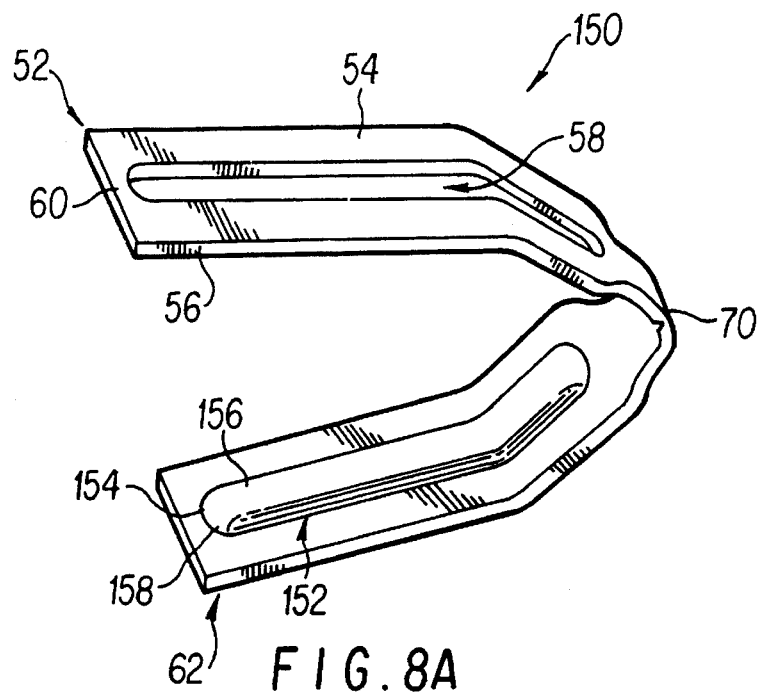
FIG. 8A illustrates the third embodiment of the invention in its normal open state.
Figure 8B:
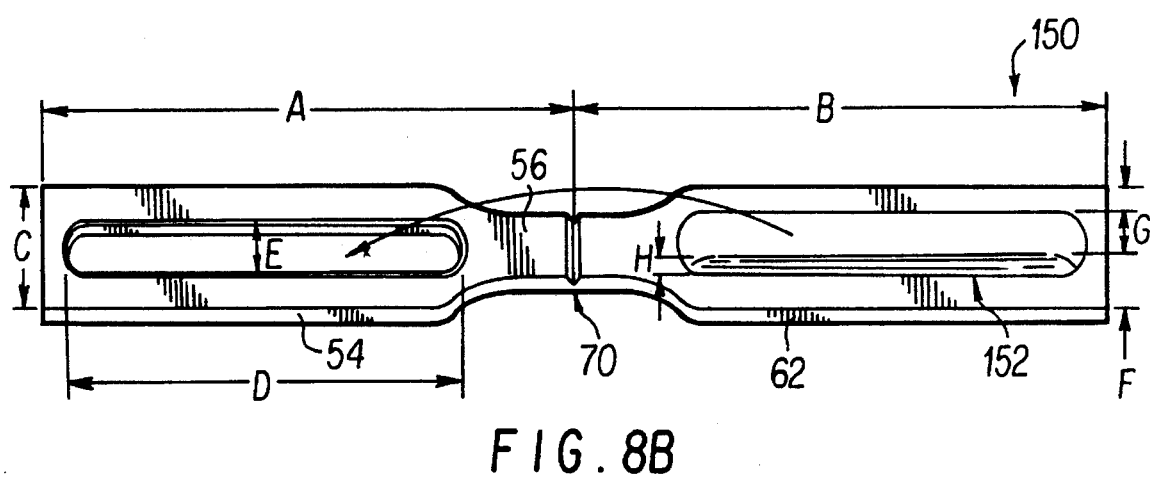
FIG. 8B illustrates the third embodiment of the invention opened to lay flat in order to illustrate the dimensions of the clip.

FIGS. 8A and 8B illustrate surgical clip 150 constructed according to the third embodiment of the invention. The clip 150 has a similar double-leg side 52 and hinge 70 as the first embodiment of the invention but the single-leg side 62 is different from the first and second embodiments. The single-leg side is constructed to have a width which is approximately equal to the width of the double-leg side. The single-leg side has a raised ridge 152 which has a rounded wedge shape which is smooth and not sharp in order to avoid cutting the tissue. The raised ridge 152 has sides 156 and 158 separated by the peak 154 of the ridge. The shape of the triangular ridge 152 is similar to the gripping shape of the single leg 62 of the first embodiment and the gripping surfaces of the double legs 156 and 158 correspond to the gripping surfaces of the single-leg 62 in the first embodiment of the invention designated by reference numerals 66 and 68. The third embodiment of the invention is referred to as the "Even Y Clip" as the width of the single-leg side 62 is equal to the width of the double-leg side 52.

FIG. 8B illustrates the third embodiment of the invention which is opened to be planar and is stretched open beyond the normal open state of the clip. The dimensions of the clip are as follows. The length A of the double leg side is 0.50" and the length B of the single leg side is 0.42". The width C of the double leg side is 0.125", the length D of the longitudinal opening is 0.220" and the width E of the longitudinal opening is 0.060". The width F of the entire single leg is 0.125". The width G of the ridge is 0.050" and the height H of the ridge is 0.017". The thickness of the double leg side and the single leg side where the ridge does not exist is 0.028" and the width of the hinged region 70 may vary from 0.045" to 0.030", depending on whether or not the hinged region narrows as illustrated in FIG. 9A.

The third embodiment of the invention may be applied to tissue in a similar manner as the first and second embodiments are applied. The clip 150 grips in a similar manner as illustrated in FIG. 5B except that the portion of the single-leg 62 other than the ridged area 152 limits the distance that the ridge 152 can extend into the opening 58.

FIGS. 9A–9D have been provided to show some of the detailed shapes of the invention. These teachings of these figures are applicable to any of the disclosed embodiments. FIG. 9A illustrates a side view of a clip 50 of the present invention. It can be seen that hinged region 70 has a narrowed waist. This narrowed waist allows the clip to be closed with less force.

FIGS. 9B and 9C illustrate the hinged region 70 respectively having a rounded indentation and a wedge-shaped or inverted V-shaped indentation. These indentations also allow the clip to be closed easier. The indentations at the hinged region 70 may either be on the inside or outside of the clip when the clip is in the closed position.

FIG. 9D illustrates a side view of a clip in its normal state having indentations 200 on both the single and double-leg sides. These indentations 200 are similar to the indentation 10 illustrated in FIG. 1. The indentations 200 provide a convenient place to hold or grip the clips during application.

FIGS. 10A–10D illustrate side views of the open state of any of the embodiments of the present invention. FIG. 10A shows a view similar to the open state of the conventional Hemoclip. FIG. 10B illustrates an embodiment where the legs are open in an unsymmetrical manner. FIG. 10C illustrates an open clip having a rounded U-shape and FIG. 10D illustrated an open clip having a sharper V-shape. Further, the open clips may have a combination of the shapes illustrated in FIGS. 10A–10D.

A test has been performed to determine the clip dislocation force in newtons of the conventional Ligaclip illustrated in FIG. 1 as compared to the three embodiments of the invention. The various clips were tested on polyethylene, and latex in sheet form. Silastic tubing was tested which is often considered a common analog for blood vessel. The size of the tubing was French 8 (8 mm in circumference) as this is approximately the size of the blood vessels that would be clipped in the course of surgery. One section of this silastic tubing was used for the second embodiment while two parallel sections were used for the Ligaclip, the first embodiment, and the third embodiment. The clips were also tested on animal blood vessels which were bovine arteries and also bovine tensor facia lata. In each test, the clips were manually placed on the substrate using needle-nosed pliers. The needle-nosed pliers is similar in concept to the manual single clip applicator used in surgery.

The substrate was rigidly clamped in series with the load cell of a gear-driven tensile-test machine (Tinius-Olsen, series 2000). The dislocating force was applied via a 0.5 mm diameter steel wire placed in the aperture of the clip and tied securely to the actuator of the testing machine. The machine was run under displacement control at a strain rate of 200 mm per minute until failure of either the clip or the substrate occurred.

There were two tests performed on the first embodiment; one test was performed with the top of the single-leg not entering the longitudinal opening but flush with the bottom of the double-legs, and the other test was performed with the single-leg entering the longitudinal opening. The test results are as follows:

| | TABLE SHOWING CLIP DISLOCATION FORCE (NEWTONS) | | | | | | | | | |
|---|---|---|---|---|---|---|---|---|---|---|
| | POLYETHYLENE | | LATEX SHEET | | SILASTIC TUBE | | ANIMAL VESSEL | | ANIMAL FASCIA | |
| CLIP | Avg | SEM | AVG | SEM | AVG | SEM | AVG | SEM | AVG | SEM |
| Ligaclip | 7.63 | 1.02 | 9.22 | 2.66 | 6.48 | 0.62 | 7.10 | 1.31 | 3.98 | 0.43 |
| 1st Embod. Flush | 9.38 | 3.52 | 5.85 | 1.19 | 14.11 | 1.24 | 15.84 | 1.44 | 3.15 | 0.24 |
| 1st Embod. Through | 4.33 | 0.77 | 8.32 | 0.21 | 21.74 | 2.02 | 21.97 | 2.44 | 3.39 | 0.10 |
| 2nd Embod. | 33.46 | 0.14 | 12.96 | 4.60 | 28.93 | 6.28 | 25.38 | 4.60 | 3.68 | 0.88 |
| 3rd Embod. | 4.45 | 1.44 | 5.73 | 1.55 | 14.89 | 1.31 | 16.57 | 0.87 | 3.49 | 0.18 |

The table shows that for the Ligaclip engaging with the vessel, the required displacement force is 7.10 plus or minus 1.31 N (mean plus or minus standard error of mean). In contrast, the first embodiment of the invention in which the single-leg did not enter the longitudinal opening of the double-leg had a displacement force which was nearly twice as high as the Ligaclip and was 15.84 plus or minus 1.44 N. Further, the first embodiment of the invention with the single-leg entering into the longitudinal opening had a displacement force of over three times the displacement force of the Ligaclip and was 21.97 plus or minus 2.44 N. The second embodiment of the invention is seen to have a displacement force of a vessel as 25.38 plus or minus 4.60 N and the third embodiment has a displacement force for the vessel as 16.57 plus or minus 0.87 N.

It is to be noted that the dislocation forces for the first and second embodiments was primarily due to the failure of the substrate being tested itself rather than a failure of the clip to hold the substrate. The test of each clip on each of the substrates being tested was performed four times.

As can be seen from the above table, the present invention provides a substantially superior gripping force than conventionally used surgical clips and are therefore a significant improvement over the commonly used and commercially available surgical clips.

The method of applying each of the first through third embodiments is as follows. The first and second sides of the clip are placed around the tissue to be clamped. The legs of the first and second sides of the clamp are squeezed together by an application device of the automatic or manual type. The squeezing of the legs causes the tissue to be pushed through the longitudinal opening by the leg of the single-leg side of the clip. Depending on the construction of the clip and the extent to which the clip is closed, the single leg may not enter the longitudinal opening, may enter the longitudinal opening but not extend through the opening, or the leg may enter and extend through the opening. Experimental applications of the clip have demonstrated that with square or rounded edges of the clamping surfaces of the legs, the present invention does not cut through tissue being clamped.

Obviously, numerous modifications and variations of the present invention are possible in light of the above teachings. It is therefore to be understood that within the scope of the appended claims, the invention may be practiced otherwise than as specifically described herein. Further, the dimensions of the clips have been given to show the preferred sizes of the clips and are not to limit the scope of the invention beyond what is recited in the claims. Further, the features and details described with respect to any one of the embodiments are applicable to the other embodiments unless contrary to the teachings of this writing or contrary to the operation of the invention.

What is claimed as new and desired to be secured by Letters Patents of the United States is:

1. A surgical clip comprising:

a first side having a first leg; and a second side having a second leg and a third leg connected to each other at a joining region at which the first leg is joined to the second and third legs, the second and third leg defining a longitudinal opening therebetween and extending through the second side;

wherein when tissue between the first leg of the first side and the second and the third legs of the second side is clamped by the surgical clip, the first leg pushes a portion of the tissue through the longitudinal opening, and at least a portion of the first leg intersects a plane defined by the second and third legs.

2. A surgical clip according to claim 1, wherein:

when the tissue is clamped by the surgical clip, the first leg is in a plane different than a plane defined by the second and third legs.

3. A surgical clip according to claim 1, wherein:

the first leg is shorter than a length between the joining region and an end of the longitudinal opening which is disposed away from the joining region.

4. A surgical clip according to claim 1, wherein:

the first leg has a width which is narrower than a width of the longitudinal opening.

5. A surgical clip according to claim 1, wherein:

the first leg is shorter than a length between the joining region and an end of the longitudinal opening which is disposed away from the joining region; and the first leg has a width which is narrower than a width of the longitudinal opening.

6. A surgical clip according to claim 5, wherein:

when the tissue is clamped by the surgical clip, a portion of the first leg extends into and through the longitudinal opening.

7. A surgical clip according to claim 1, wherein:

clip is displaced to another plane by the surgical clip, the plane of the tissue is displaced by an interaction of the first leg with the second and third legs.

8. A surgical clip according to claim 1, wherein:

the second leg and third leg are connected both at the region where the second and third legs are connected to the first leg, and at ends of the second and third legs which are disposed away from the region at which the second and third legs are connected to the first leg.

9. A surgical clip according to claim 1, wherein:

the first leg includes a raised ridge for dividing a surface for gripping the tissue longitudinally into two halves.

10. A surgical clip according to claim 9, wherein:

one half of the first leg engages with and corresponds to the second leg, and the other half of the first leg engages with and corresponds to the third leg; and surfaces on each of the second and third legs for gripping the tissue are angled to be parallel to the corresponding surface of the first leg.

11. A surgical clip according to claim 1, wherein:

edges of gripping surfaces of each of the first, second, and third legs are square.

12. A surgical clip according to claim 1, wherein:

a width of the first side of the surgical clip is greater than a width of the longitudinal opening; and a tissue gripping side of the first leg includes a raised ridge disposed along a length of the first leg.

13. A surgical clip according to claim 1, wherein:

a locking of the surgical clip in a closed state is a bending of the surgical clip.

14. A surgical clip according to claim 1, wherein:

a locking of the surgical clip in a closed state is a bending of the joining region when the first side and second side are moved towards each other.

15. A surgical clip according to claim 1, wherein:

said surgical clip is a unitary device.

16. A surgical clip according to claim 1, wherein:

said clip comprises material selected from one of stainless steel and titanium.

17. A surgical clip for clamping tissue, the clip having an open state and a closed state, comprising:

first and second sides joined together at their proximal ends at a hinged region, said first side having a longitudinal opening therethrough to define first and second legs which are joined at their proximal ends to each other, said second side having a longitudinal protruding zone that defines a third leg, said third leg being spaced from said first and second legs when the clip is in the open state, said third leg extending into said longitudinal opening when the clip is in the closed state, wherein when the clip is in the closed state the tissue clamped between said third leg and said first and second legs extends through said longitudinal opening, and tissue held in said closed state by the clip is compressed between said first leg and said second leg as well as between said first leg and said third leg.

18. The surgical clip of claim 17, wherein:

said third leg has a cross-sectional area that is approximately triangular to provide first and second tissue contact walls, and wherein said first and third legs have inboard walls that provide third and fourth tissue contact walls, the spatial orientation of said third and fourth walls matching the orientation of said first and second walls respectively when in said closed state, said clip when moved from its open state to its closed state providing a wedging action to force tissue through said longitudinal opening prior to the end state compression of tissue between the walls of said third leg and the facing walls of said first and second legs.

19. The surgical clip of claim 17, wherein:

said clip is a unitary device.

20. The surgical clip of claim 17, wherein:

said clip is composed of materials from the group consisting of surgical stainless steel and titanium.

21. The surgical clip of claim 17, wherein:

said first and second legs are joined to each other at their distal ends.

22. The surgical clip of claim 17, wherein:

said third leg extends into and through said longitudinal opening when the clip is in its closed state.

* * * * *